(12) United States Patent
Schmidt et al.

(10) Patent No.: US 10,898,609 B2
(45) Date of Patent: Jan. 26, 2021

(54) TISSUE DECELLULARIZATION METHODS

(71) Applicant: University of Florida Research Foundation, Inc., Gainesville, FL (US)

(72) Inventors: Christine E. Schmidt, Gainesville, FL (US); Rebecca Ann Wachs, Lincoln, NE (US); Robert Chase Cornelison, Charlottesville, VA (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 223 days.

(21) Appl. No.: 15/744,942

(22) PCT Filed: Jul. 14, 2016

(86) PCT No.: PCT/US2016/042273
§ 371 (c)(1),
(2) Date: Jan. 15, 2018

(87) PCT Pub. No.: WO2017/011653
PCT Pub. Date: Jan. 19, 2017

(65) Prior Publication Data
US 2018/0207318 A1    Jul. 26, 2018

Related U.S. Application Data

(60) Provisional application No. 62/192,823, filed on Jul. 15, 2015.

(51) Int. Cl.
*A61L 27/36* (2006.01)
*C12N 5/0793* (2010.01)
(Continued)

(52) U.S. Cl.
CPC .......... *A61L 27/3633* (2013.01); *A61K 35/30* (2013.01); *A61K 35/32* (2013.01);
(Continued)

(58) Field of Classification Search
None
See application file for complete search history.

(56) References Cited

U.S. PATENT DOCUMENTS 5,968,824 A    10/1999  Spruce et al.
9,216,236 B2 * 12/2015  Machluf ............ A61L 27/3633
(Continued)

FOREIGN PATENT DOCUMENTS

WO    98/31787    7/1998
WO    98/45429    10/1998

OTHER PUBLICATIONS

Morris, Erick J., and Herbert M. Geller. "Induction of neuronal apoptosis by camptothecin, an inhibitor of DNA topoisomerase-I: evidence for cell cycle-independent toxicity." The Journal of cell biology 134.3 (1996): 757-770. (Year: 1996).*
(Continued)

*Primary Examiner* — Robert J Yamasaki
(74) *Attorney, Agent, or Firm* — Thomas|Horstemeyer LLP

(57) ABSTRACT

Provided herein are methods of producing an acellular tissue product wherein the method can include the step of inducing apoptosis and washing the tissue after induction of apoptosis with a tonic solution. Also provided herein are acellular tissue products produced by the methods provided herein and methods of administering the acellular tissue products to a subject in need thereof.

13 Claims, 8 Drawing Sheets

(51) Int. Cl.
  *A61K 35/30* (2015.01)
  *A61K 35/42* (2015.01)
  *A61K 35/32* (2015.01)
  *A61L 27/54* (2006.01)

(52) U.S. Cl.
  CPC .......... *A61K 35/42* (2013.01); *A61L 27/3687* (2013.01); *A61L 27/54* (2013.01); *C12N 5/0619* (2013.01); *A61L 2430/40* (2013.01); *C12N 2533/90* (2013.01)

(56) References Cited

U.S. PATENT DOCUMENTS

| | | | |
|---|---|---|---|
| 2003/0219417 A1 | 11/2003 | Wolfinbarger | |
| 2005/0009000 A1* | 1/2005 | Wilhelm | A01N 1/00 435/1.1 |
| 2008/0306610 A1 | 12/2008 | Wang et al. | |
| 2011/0045045 A1 | 2/2011 | Cortiella et al. | |
| 2012/0259415 A1 | 10/2012 | Van Dyke et al. | |
| 2015/0037436 A1 | 2/2015 | Huang et al. | |

OTHER PUBLICATIONS

Zhao, Zhe, et al. "Improvement in nerve regeneration through a decellularized nerve graft by supplementation with bone marrow stromal cells in fibrin." Cell transplantation 23.1 (2014): 97-110. (Year: 2014).*

International Search Report for PCT/US2016/042273 dated Sep. 30, 2016.

Bourgine, et al., "Tissue decellularization by activation of programmed cell death", Biomaterials 34, 2013, 6099-6108.

Vasudevan, et al. Detergent-free Decellularized Nerve Grafts for Long-gap Peripheral Nerve Reconstruction. PRSGO 2(8), 2014, 1-8.

Hudson, et al. Engineering an Improved Acellular Nerve Graft via Optimized Chemical Processing. Tissue Engineering 10(9/10), 2004, 1346-1358.

Bourgine, et al. Osteoinductivity of engineered cartilaginous templates devitalized by inducible apoptosis. PNAS 111(49), 2014, 17426-17431.

* cited by examiner

FIG. 2A Fresh Nerve — Nuclei, Neurons, Schwann cells

FIG. 2B Hypertonic + Hypotonic — 5 µM, 1 DIV — 100 µm

FIG. 2C Hypertonic + DNase — 5 µM, 1 DIV — 100 µm

FIG. 2D Fresh Nerve+Wash — 100 µm

FIG. 2E Hypertonic + Hypotonic — 10 µM, 1 DIV — 100 µm

FIG. 2F Hypertonic + DNase — 10 µM, 1 DIV — 100 µm

| ng/mg | 1500.0 | 1052.7 | 420.9 | 640.0 | | 73.4 | 63.2 |
|---|---|---|---|---|---|---|---|
| % Removal | -- | 29.8 | 71.9 | 57.3 | | 95.1 | 95.8 |

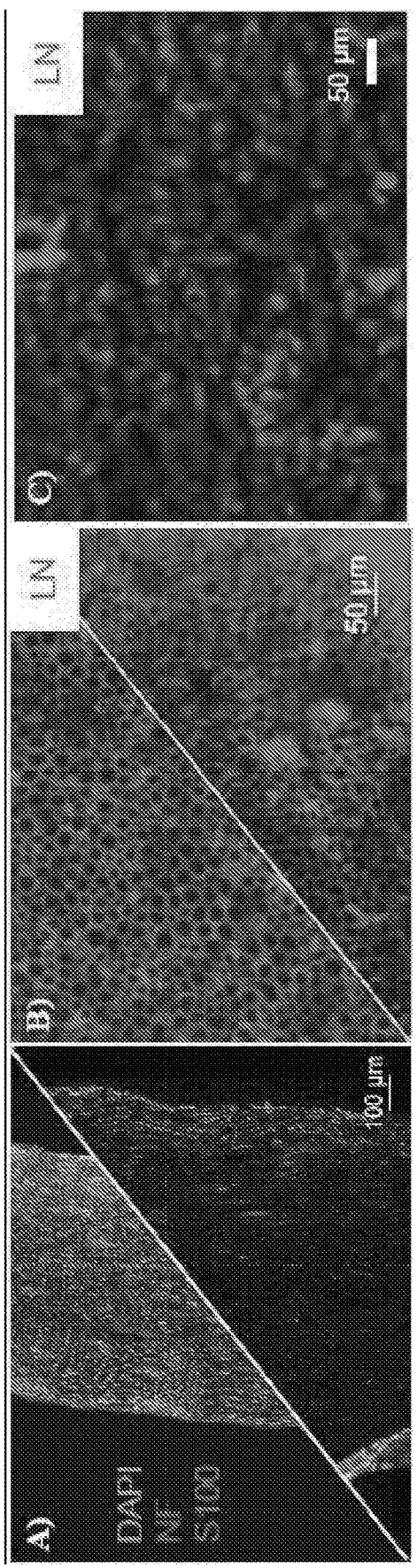

Fresh Nucleus Pulposus
FIG. 6A

Cell Nuclei
Proteoglycans
100 μm

FIG. 6B

10 μM, 1 DIV

Control

Hypertonic

Nucleus Pulposus Isolation

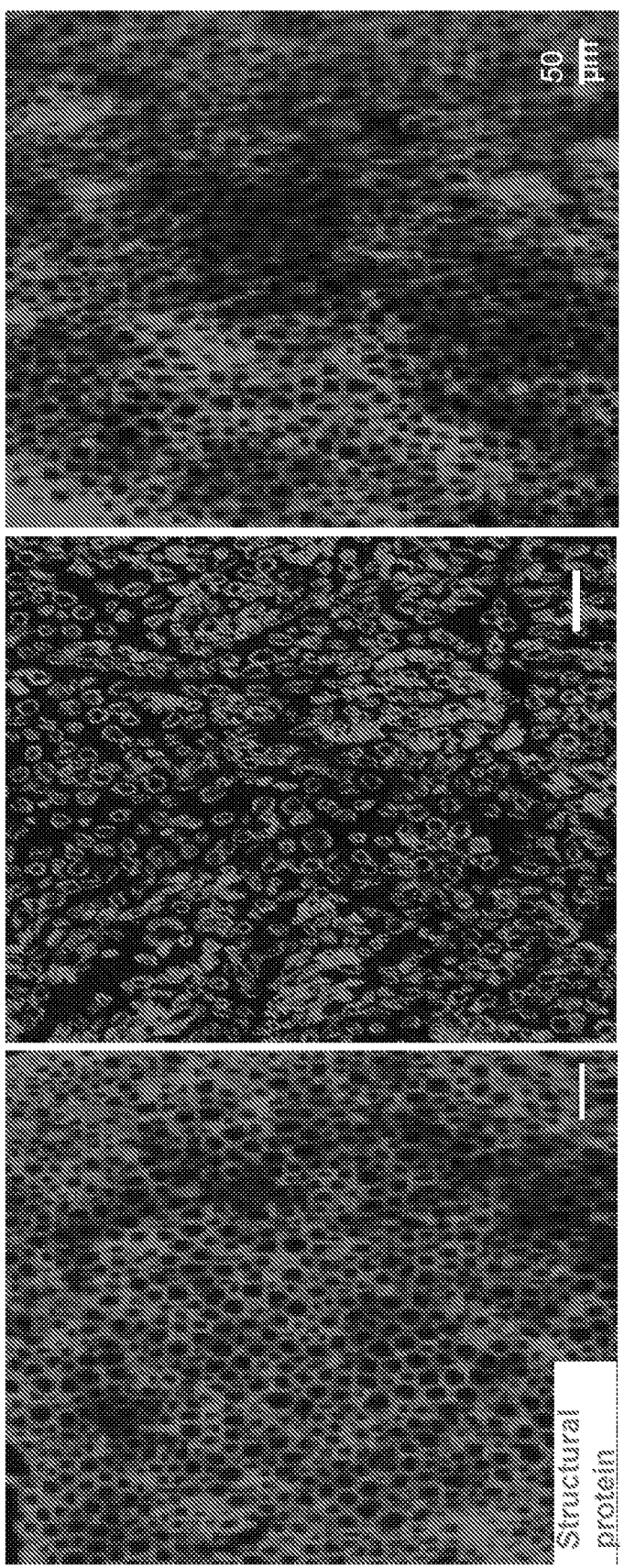
FIG. 9A Fresh Nerve
FIG. 9B Treatment with Water
FIG. 9C Apoptosis Decellularization

TISSUE DECELLULARIZATION METHODS

CROSS-REFERENCE TO RELATED APPLICATIONS

This application is the 35 U.S.C. § 371 national stage application of PCT Application No. PCT/US2016/042273, filed Jul. 14, 2016, where the PCT claims the benefit of and priority to U.S. Provisional Patent Application No. 62/192,823, filed on Jul. 15, 2015, entitled "TISSUE DECELLULARIZATION METHODS," both of which are herein incorporated by reference in their entireties.

GOVERNMENT FUNDING

This invention was made with government support under R21 EB013358 awarded by National Institutes of Health. The government has certain rights in the invention.

BACKGROUND

Decellularization technology offers the potential to attain tissue-specific scaffolds that guide tissue regeneration following injury and/or disease. As such there exists a need for improved decellularization methods for scaffold generation for tissue regeneration for treatment of injury and/or disease.

SUMMARY

Provided herein are tissue decellularization methods, where the methods can include the steps of obtaining a tissue sample from a subject to generate an ex vivo tissue sample; exposing the ex vivo tissue sample to an apoptotic agent or apoptotic process; and washing the ex vivo tissue sample in a hypertonic solution, a hypotonic solution, or a hypertonic solution and a hypotonic solution. The tissue sample can be a peripheral nerve, a nucleus pulposus, and/or a combination thereof. The tissue sample can be a lung tissue. The apoptotic agent is camptothecin, staurosporine, doxorubicin, or an analog thereof. The apoptotic process can contain one or more freeze-thaw cycles. The concentration of the apoptotic agent can range from about 5 µM to about 10 µM. The concentration of the apoptotic agent can be about 10 µM. The concentration of the apoptotic agent can be about 5 µM. The ex vivo tissue sample can be exposed to the apoptotic agent for about 2 days. The tissue can be washed with a hypertonic solution. The hypertonic solution can be greater than 1× buffered solution. The hypertonic solution is 4× saline. The tissue can be washed with a hypotonic solution. The hypotonic solution can less than 1× buffered solution. The hypotonic solution can be a 0.5× saline solution. The concentration the concentration of the apoptotic agent can be about 5 µM. The apoptotic agent can be camptothecin, staurosporine, doxorubicin, or an analog thereof. The method can further include the step of treating the tissue with DNAse for a period of time ranging from 30 minutes to 24 hours. The step of washing can produce an acellular tissue product. The method can further include step of adding an active agent to the acellular tissue product. The active agent can selected from the group consisting of: a stem cell, nucleic acid, amino acid, peptide, polypeptide, antibody, aptamer, ribozyme, guide sequence for a ribozyme that inhibit translation or transcription of essential tumor proteins and genes, hormone, immunomodulator, antipyretic, anxiolytic, antipsychotic, analgesic, antispasmodic, anti-inflammatory, anti-histamine, anti-infective, a chemotherapeutic, or combinations thereof.

Also provided herein are acellular tissue products, where the acellular tissue product can be formed by a method as described herein. The method can further include the step of treating the tissue with DNAse for a period of time ranging from about 30 minutes to about 24 hours. The acellular tissue product can contain an active agent. The active agent can be selected from the group consisting of: a stem cell, nucleic acid, amino acid, peptide, polypeptide, antibody, aptamer, ribozyme, guide sequence for a ribozyme that inhibit translation or transcription of essential tumor proteins and genes, hormone, immunomodulator, antipyretic, anxiolytic, antipsychotic, analgesic, antispasmodic, anti-inflammatory, anti-histamine, anti-infective, a chemotherapeutic, or combinations thereof. The acellular tissue product can be formulated for injection.

Also provided herein are methods including the step of administering an acellular tissue product as provided herein to a subject in need thereof. The subject in need thereof can have a spinal injury or disease, intervertebral disc degeneration, disease or trauma of the lungs or liver, or volumetric muscle loss, peripheral nerve injury, amputation or spinal degradation, osteoarthritis of the hip or knee, volumetric muscle loss, cirrhosis of the liver, or otherwise requires partial or total organ replacement.

BRIEF DESCRIPTION OF THE DRAWINGS

Further aspects of the present disclosure will be readily appreciated upon review of the detailed description of its various embodiments, described below, when taken in conjunction with the accompanying drawings.

FIGS. 2A-2F show fluorescence micrographs of peripheral nerve with and without apoptosis induction followed by washing with various regimens.

FIGS. 5A-5C demonstrate fluorescence micrographs of nerve tissue labeled for cell or basal lamina markers. For FIGS. 5A and 5B, the images are fresh nerve (top half) and apoptosis decellularized nerve (bottom half). FIG. 5A was labeled for neurons (neurofilament, green), Schwann cells (S100, red), and nuclei (DAPI, blue). FIG. 5B shows cross-sections of the basal lamina stained for laminin (red). FIG. 5C shows a representative basal lamina staining in nerve tissue decellularized according to a conventional detergent-based method.

FIGS. 6A-6D demonstrate fluorescence micrographs of nucleus pulposus stained with a nuclear stain (blue) and a chondroitin sulfate proteoglycan (CSPG) antibody (red).

FIGS. 9A-9C show fluorescence images demonstrating that the more gentle apoptosis decellularization (FIG. 9C)

Figure 1:
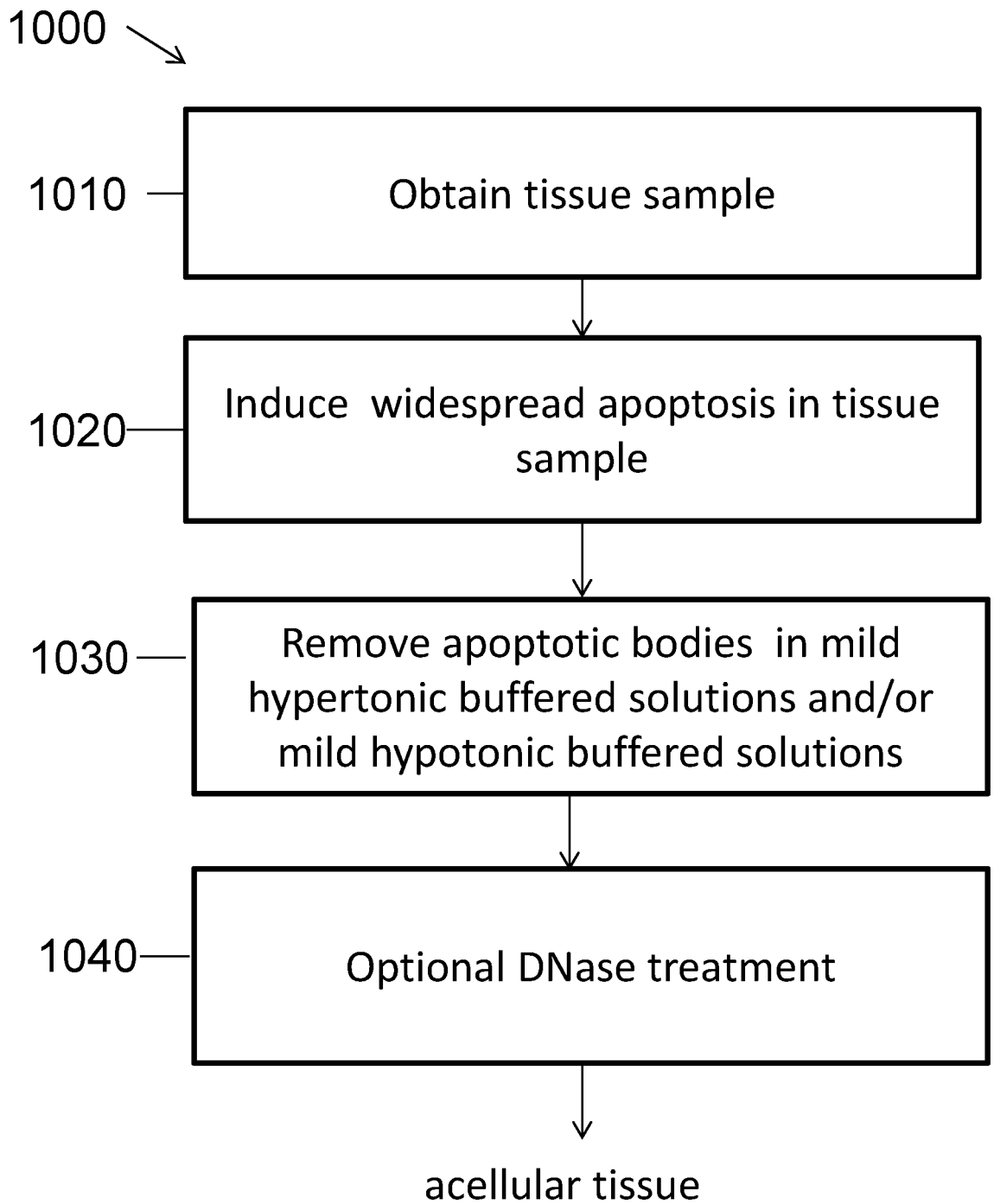
FIG. 1 shows one embodiment of a method for decellularization of a tissue sample.

process can result in less tissue disruption than the harsher traditional decellularization methods which uses a water treatment to initiate decellularization (FIG. 9B), and more comparable to fresh nerve (FIG. 9A).

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

As used herein, "about," "approximately," and the like, when used in connection with a numerical variable, generally refers to the value of the variable and to all values of the variable that are within the experimental error (e.g., within the 95% confidence interval for the mean) or within ±10% of the indicated value, whichever is greater.

As used herein, "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" includes but is not limited to, subcutaneous, intravenous, intramuscular, intra-articular, intra-synovial, intrasternal, intrathecal, intrahepatic, intralesional, and intracranial injections or infusion techniques.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "control" is an alternative subject or sample used in an experiment for comparison purposes and included to minimize or distinguish the effect of variables other than an independent variable.

As used herein, "positive control" refers to a "control" that is designed to produce the desired result, provided that all reagents are functioning properly and that the experiment is properly conducted.

As used herein, "negative control" refers to a "control" that is designed to produce no effect or result, provided that all reagents are functioning properly and that the experiment is properly conducted. Other terms that are interchangeable with "negative control" include "sham," "placebo," and "mock."

As used herein, "autologous" refers to being derived from the same subject that is the recipient.

As used herein, "allograft" refers to a graft that is derived from one member of a species and grafted in a genetically dissimilar member of the same species.

As used herein "xenograft" or "xenogeneic" refers to a substance or graft that is derived from one member of a species and grafted or used in a member of a different species.

As used herein, "autograft" refers to a graft that is derived from a subject and grafted into the same subject from which the graft was derived.

As used herein, "allogeneic" refers to involving, derived from, or being individuals of the same species that are sufficiently genetically different so as to interact with one another antigenically.

As used herein, "donor" refers to a subject from which cells or tissues are derived.

As used herein, "hypertonic solution" refers to a solution that has a greater concentration of solutes than the concentration of solutes inside of a cell.

As used herein, "hypotonic solution" refers to a solution that has a concentration of solutes that is less than the concentration of solutes within a cell.

As used herein, "analog" refers to another compound, composition, or other substance of matter that is considered comparable to the reference compound, composition, or substance of matter and includes structural analogs and functional analogs.

Discussion

Decellularization technology offers the potential to attain tissue-specific scaffolds that guide tissue regeneration following injury and/or disease. Most decellularization protocols used in research and industry contain an initial cell lysis step in a hypotonic buffer, such as water, followed by chemical solutions to remove cellular remnants. These harsh conditions result in an undesirable broad dispersal of intracellular components, disruption of tissue morphology, and removal of desired tissue elements.

With that said, described herein are decellularization methods that do not require cell lysis buffers or harsh chemicals. The decellularization methods described herein can include inducing apoptosis in ex vivo tissue. The decellularization methods described herein can effectively remove cellular components without having to rely on harsh conditions. In some embodiments, the methods can effectively remove cellular components from peripheral nerve and/or nucleus pulposus. In addition to reducing time, labor, and expense of decellularization, some embodiments described herein can only need one step for inducing apoptosis and one step for washing the cells.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Methods

Described herein are methods of decellularization that include inducing apoptosis in an ex vivo tissue sample, where tissue wide apoptosis can be induced by exposing the tissue to an apoptosis-inducing agent or apoptosis inducing process for a time period. Induction of apoptosis in the ex vivo tissue sample can cause cell detachment from the tissue extracellular matrix, degradation of intracellular DNA, RNA and proteins, and allocation into apoptotic bodies, which can be removed using mild hypotonic and/or mild hypertonic buffered solutions.

As shown in FIG. 1, the method 1000 can begin with obtaining a tissue sample from a subject or other donor source 1010. The tissue can be autologous, xenogeneic, allogeneic, or syngeneic. In some embodiments, the tissue can be obtained from anywhere in a subject. In some embodiments, the tissue sample can be obtained from the periphery or spinal column of a subject. In some embodiments, the tissue can be a peripheral nerve and/or nucleus pulposus. In other embodiments, the tissue can be brain, spinal cord, heart, lung, liver, muscle, cartilage, tendons, ligaments, menisci, stomach, intestine, pancreas, and/or kidney. In further embodiments, the tissue is blood vessels, bone, and/or cornea.

After the tissue sample has been obtained, apoptosis can be induced 1020 in the ex vivo tissue sample by exposing the ex vivo tissue sample to an apoptotic agent (i.e. a compound and/or composition that induces apoptosis in a cell) for a time period. In some embodiments, apoptosis can be induced by an apoptotic process (i.e. a process that can include one or more steps that induces apoptosis). In some embodiments, the apoptotic agent can be camptothecin, staurosporine, doxorubicin, and/or analogs thereof, or any other agent or process that induces apoptosis. In other embodiments, the apoptotic agent could be nitric oxide, hypoxia, pH, or hydrogen peroxide. In some embodiments where an apoptotic agent is used to induce apoptosis, the ex vivo tissue sample can be exposed to the apoptotic agent for any length of time, including but not limited to, greater than about 1 hour, about 1 hour to about 10 days, about 1 hour to about 7 days, about 1 hour to about 4 days, about 1 hour to about 2 days, or about 1 hour to about 1 day. In some embodiments, the ex vivo tissue sample can be exposed to camptothecin or analog thereof for 2 days. In some embodiments, the tissue ex vivo tissue sample can be exposed to the apoptotic agent, such as camptothecin, for about 1 day.

The ex vivo tissue sample can be exposed to a solution containing a concentration of the apoptotic agent and/or to an apoptotic process. In some embodiments, the apoptotic process does not use an apoptotic agent. In embodiments that employ an apoptotic agent, the concentration of the apoptotic agent can range from about 1 nM to about 1 mM or greater. In some embodiments, the concentration of the apoptotic agent can range from about 1 µM to about 100 µM. In some embodiments, the concentration of the apoptotic agent can be about 10 µM. In some embodiments, the ex vivo tissue sample can be exposed to 10 µM of camptothecin or an analog thereof. In some embodiments, the ex vivo tissue sample can be exposed to 10 µM of camptothecin or an analog thereof for about 2 days. In some embodiments, the concentration of the apoptotic agent can range from about 5 µM to about 10 µM. In some embodiments, the concentration of the apoptotic agent is about 5 µM. In some embodiments, the ex vivo tissue sample can be exposed to 5 µM camptothecin or an analog thereof. In some embodiments, the ex vivo tissue sample can be exposed to 5 µM of camptothecin or an analog thereof for about 1 day.

In some embodiments, the apoptotic process includes exposure of the ex vivo tissue to one or more freeze-thaw cycles to induce apoptosis.

After the ex vivo tissue sample can be exposed to an apoptotic agent or process for a desired amount of time, the tissue sample can be washed 1030 with one or more washes with one or more buffered solutions to facilitate cell removal. The ex vivo tissue sample can be washed with one or more washes of a hypertonic buffered solution (i.e. greater than 1× buffered solution). In some embodiments the number of washes ranges from one to six. In some embodiments, the hypertonic solution can be a 1.01×-10× buffered solution. In some embodiments, the concentration can be 4× with an intermediate 2× wash. The tissue sample can be washed with one or more washes of a hypotonic buffered solution (i.e. less than 1× buffered solution). In some embodiments, the hypotonic solution can be a 0.01× up to a 0.99× buffered solution. In embodiments, the buffered solution is a saline solution at the given concentrations to result in a hypotonic or hypertonic solution. The starting saline solution can be isotonic. The starting saline solution can have a formulation of 10× which is diluted with water to attain various hypertonic washes. While not being bound to theory, it is believed that DNA removal occurs under the hypotonic wash conditions, while protein removal occurs under the hypertonic wash conditions. Some embodiments employ only hypertonic washes. Other embodiments employ only hypotonic washes. Yet further embodiments employ both hypertonic and hypotonic washes.

In some embodiments, the method 1000 can also include an optional step of DNAse treatment 1040. The DNAse treatment can occur after the wash(es) previously performed 1030. In some embodiments, the optional DNAse treatment 1040 is performed after hypotonic washes 1030 were performed. In some embodiments where the optional DNAse 1040 treatment is performed, only hypertonic washes have been performed. In embodiments, the concentration of DNAse can range from 25 U/mL to 250 U/mL. The preferred concentration is 75 U/mL. The DNase can be any suitable DNase. The DNase treatment can be performed at a temperature ranging from about 4 to about 37° C. The preferred temperature is 25° C. It will be appreciated by those of ordinary skill in the art that the temperature can be dependent on the temperature that the DNase has optimal activity. The time period for the DNase treatment can range from about 30 minutes or less to 1, 2, 3, 4, 5, 6, 7, 8, 9, 10, 11, 12, 24, or 36 hours or more. The treatment time can vary based on tissue type, but in some embodiments the treatment time is 18-24 hours.

The method 1000 can produce an acellular tissue. The resulting acellular tissue can be used as a scaffold substrate for three dimensional (3D) cell culture and tissue engineering techniques. Further, the resulting acellular tissue can be delivered to a subject in need thereof to facilitate the in vivo generation and/or regeneration of cells and tissues within the subject. The resulting acellular tissue product can be formulated to be delivered to a subject in need thereof by any suitable method of deliver, including but not limited to, implantation or injection. The acellular tissue products can be enhanced by the addition of one or more other agents or compounds to the acellular tissue product, including without limitation other cells (e.g. stem cells or other progenitor cells), nucleic acids, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics. In some embodiments, the acellular tissue products can be co-administered with one or more other agents or compounds, including without limitation other cells (e.g. stem cells or other progenitor cells), nucleic acids, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

In some embodiments, any of the acellular tissue scaffolds described herein can be administered to a subject in need thereof in the original form, as an injectable formulation, or as other derivatives of the acellular tissue. In some embodiments, the subject in need thereof has a peripheral nerve injury, spinal cord injury, spinal cord disease, amputation or otherwise suffers from degradation of a component of the spine (e.g. intervertebral disc degeneration). In other embodiments, the subject could have osteoarthritis of the hip or knee, trauma to the lungs, volumetric muscle loss, cirrhosis of the liver, or otherwise requires partial or total organ replacement.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Peripheral nerves were harvested from Sprague Dawley rats and decellularized according to an apoptosis-assisted protocol using 5 µM camptothecin in non-supplemented media at 37° C. for 1 day. Tissue in media without camptothecin, an apoptotic agent, was used as a control. Apoptotic agent treatment was succeeded by washes in saline buffered solutions to optimize cell removal. Furthermore, the tissue was treated with 75 u/mL DNAse for 24 hours to ensure DNA removal. The degree of apoptosis, cellular removal, and matrix preservation was assessed using immunochemistry on nerve tissue sections and fluorescence imaging (FIG. 2). Antibodies used to identify apoptosis, cell removal, and tissue preservation include those against active caspase 3 (Abcam); neurofilament (RT-97, DSHB) and S100 (Dako); and laminin (Sigma), respectively. FIG. 2A shows immunochemical staining of a fresh peripheral nerve used as a no treatment control. FIGS. 2B and 2C show nerves treated with 5 µM for 1 day, washed with a hypertonic, and either washed with a hypertonic solution or treated for 24 hours with DNAse, respectively. FIG. 2D shows staining of a fresh nerve that was subjected to the same hypertonic and hypotonic washes and represents the results of not inducing apoptosis prior to washing the tissue. FIGS. 2E and 2F show treatment with higher camptothecin (10 µM), again for 1 day, and washed similarly to tissue in FIGS. 2B and 2C. These images depict 1) apoptosis induction is necessary prior to washing to effectively remove cellular components and 2) combing apoptosis induction with washes in non-isotonic solutions achieves cellular removal of peripheral nerve tissue.

Figures 3, 4:
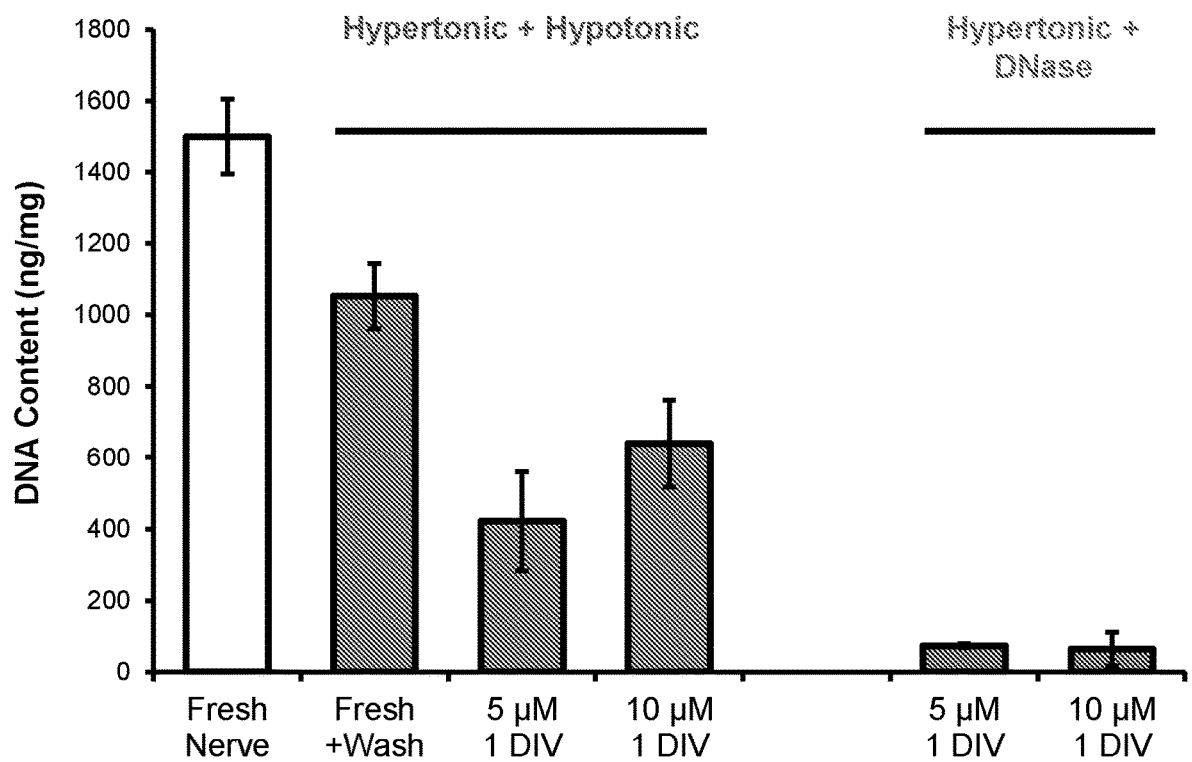
FIG. 3 shows a graph demonstrating DNA content of peripheral nerve under various treatment regimens.
FIG. 4 shows a table demonstrating the quantification of DNA content shown in FIG. 3.

Total DNA content was quantified using a Picogreen DNA assay (Life Technologies) according to manufacturer's instructions. DNA quantification data are shown in FIGS. 3 and 4. Washing the tissue without first inducing apoptosis resulted in only a 29.8% reduction of DNA content compared to fresh nerve. Conversely, inducing apoptosis using 5 or 10 µM camptothecin yielded a 71.9 and 57.3% reduction in DNA, respectively. Replacing the hypotonic wash with DNAse treatment further reduced the DNA content, with 5 and 10 µM camptothecin treatment for 1 day resulting in a 95.1 and 95.8% reduction.

Example 2

Peripheral nerves were harvested from Sprague Dawley rats and decellularized according to an apoptosis-assisted protocol using 10 µM camptothecin in non-supplemented media at 37° C. for 2 days. Tissue in media without camptothecin was used as a control. Apoptotic agent treatment was succeeded by washes in saline buffered solutions to optimize cell removal. The degree of apoptosis, cellular removal, and matrix preservation was assessed using immunochemistry on nerve tissue sections and fluorescence imaging. Antibodies used to identify apoptosis, cell removal, and tissue preservation include those against active caspase 3 (Abcam); neurofilament (RT-97, DSHB) and S100 (Dako); and laminin (Sigma), respectively. Apoptosis-mediated DNA fragmentation was assessed using a terminal deoxynucleotidyl transferase dUTP nick end labeling (TUNEL) assay. Total DNA content was quantified using a Picogreen DNA assay (Life Technologies) according to manufacturer's instructions.

FIGS. 5A-5C demonstrate fluorescence micrographs of nerve tissue labeled for cell or basal lamina markers. For FIGS. 5A and 5B, the images are fresh nerve (top half) and apoptosis decellularized nerve (bottom half). FIG. 5A was labeled for neurons (neurofilament, green), Schwann cells (S100, red), and nuclei (DAPI, blue). FIG. 5B shows cross-sections of the basal lamina stained for laminin (red). FIG. 5C shows a representative basal lamina staining in nerve tissue decellularized according to a conventional detergent-based method. Induction of apoptosis was confirmed in treated nerve tissue by an increase in active caspase 3, an early mediator of apoptosis. Moreover, TUNEL staining revealed pervasive DNA fragmentation in treated nerves, indicating late stage apoptosis, as well. Media controls exhibited neither hallmark of apoptosis. Following induction of apoptosis, cellular proteins were easily removed using only washes in hypertonic 4× saline buffer while removal of DNA required brief washes in mildly hypotonic 0.5× saline buffer. Using this regimen, a substantial reduction in cellular and nuclear staining was achieved compared to fresh nerve. Notably, the basal lamina microstructure was nearly identical to fresh nerve and was significantly improved over alternatively processed tissue.

Treatment with camptothecin was observed to be sufficient to elicit aspects of apoptosis ex vivo, including caspase 3 activation and DNA fragmentation. Moreover, induction of apoptosis was observed to enable extensive removal of cellular and nuclear components from peripheral nerve tissue using only non-isotonic buffers. Two analogs of camptothecin are considered safe by the FDA, which bolsters the clinical potential of this apoptosis-assisted decellularization method. Ultimately, the approach demonstrated here and described herein can eliminate the need for harsh lysis and chemical steps in conventional protocols and pushes decellularization technology toward achieving 3D, cell-free replicas of native tissue.

Example 3

Figure 7B:
FIGS. 7A-7B demonstrate images of a carefully dissected motion segment of the spine and an extracted nucleus pulposus.
Figure 7A:
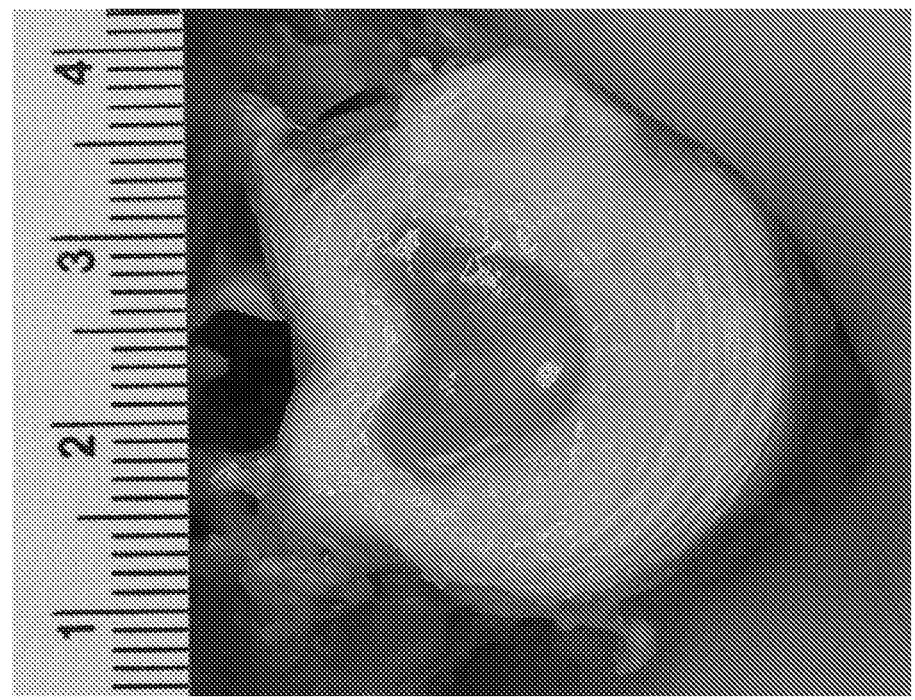

Cervical and lumbar segments were removed Yorkshire-Landrace porcine. Each motion segment was carefully dissected to extract the nucleus pulposus as shown in FIG. 7. Nucleus pulposi were decellularized according to an apoptosis-assisted protocol using 10 μm camptothecin in standard non-supplemented culture media for 24 hours. Control samples were also processed in parallel without camptothecin. After induction of apoptosis, samples were washed in a series of hypertonic and hypotonic buffers to remove apoptotic cell bodies (Table 1).

TABLE 1

| Wash Type | Method |
| --- | --- |
| Hypertonic | 2X PBS 30 min, 4X PBS 18 hrs, 2X PBS 30 min, 1X PBS 30 min |
| Hypotonic | 0.5X PBS 18 hrs, 1X PBS 30 min |
| Hyper-Hypo | 2X PBS 30 min, 4X PBS 18 hrs, 2X PBS 30 min, 1X PBS 30 min, 0.5X PBS 6 hr, 1X PBS 30 min |
| Hypo-Hyper | 0.5X PBS 18 hrs, 1X PBS 30 min, 2X PBS 30 min, 4X PBS 6 hrs, 2X PBS 30 min, 1X PBS 30 min |
| Hyper-DNase | 2X PBS 30 min, 4X PBS 18 hrs, 2X PBS 30 min, 1X PBS 30 min, 24 hrs DNase, 1X PBS 45 mins |
| No Wash | Fix Immediately after 24 hrs in media. |

After washes, samples were processed for fixed and stained using DAPI (ThermoFisher, D1306) to detect removal of cell nuclei, and a chondroitin sulfate proteoglycan (CSPG) antibody (Sigma, C8035) to examine maintenance of key proteins. Confocal imaging was used to assess removal of cell nuclei and maintenance of CSPGs. Results demonstrated in FIGS. 6A-6D suggest the hypertonic wash and the hypertonic-hypotonic wash substantially remove cell nuclei while maintaining desired CSPGs.

Example 4

Rat sciatic nerve was isolated from Sprague Dawley rats and decellularized using either standard detergent-based methods or apoptosis induction and tonic wash methods as detailed in Example 1 above. A rat transection model of nerve injury was performed in Lewis rats to determine efficacy of apoptosis decellularized samples compared to detergent decellularized samples, fresh harvested Lewis isograft sciatic nerves, and a sham control group. Briefly, sciatic nerve was transected and 8 mm of sciatic nerve was then removed to create a 10 mm nerve gap. After transection, one of three samples was implanted via direct suture to the nerve stumps (detergent, apoptosis, or isograft). Implants and sham controls were harvested at 4 weeks (n=3) and 8 weeks (n=6) for histological analysis. Tibialis anterior muscles were also harvested and weighed at 4 and 8 weeks to determine degree or re-innervation of a distal target, an indirect assessment of regeneration.

Figure 8:
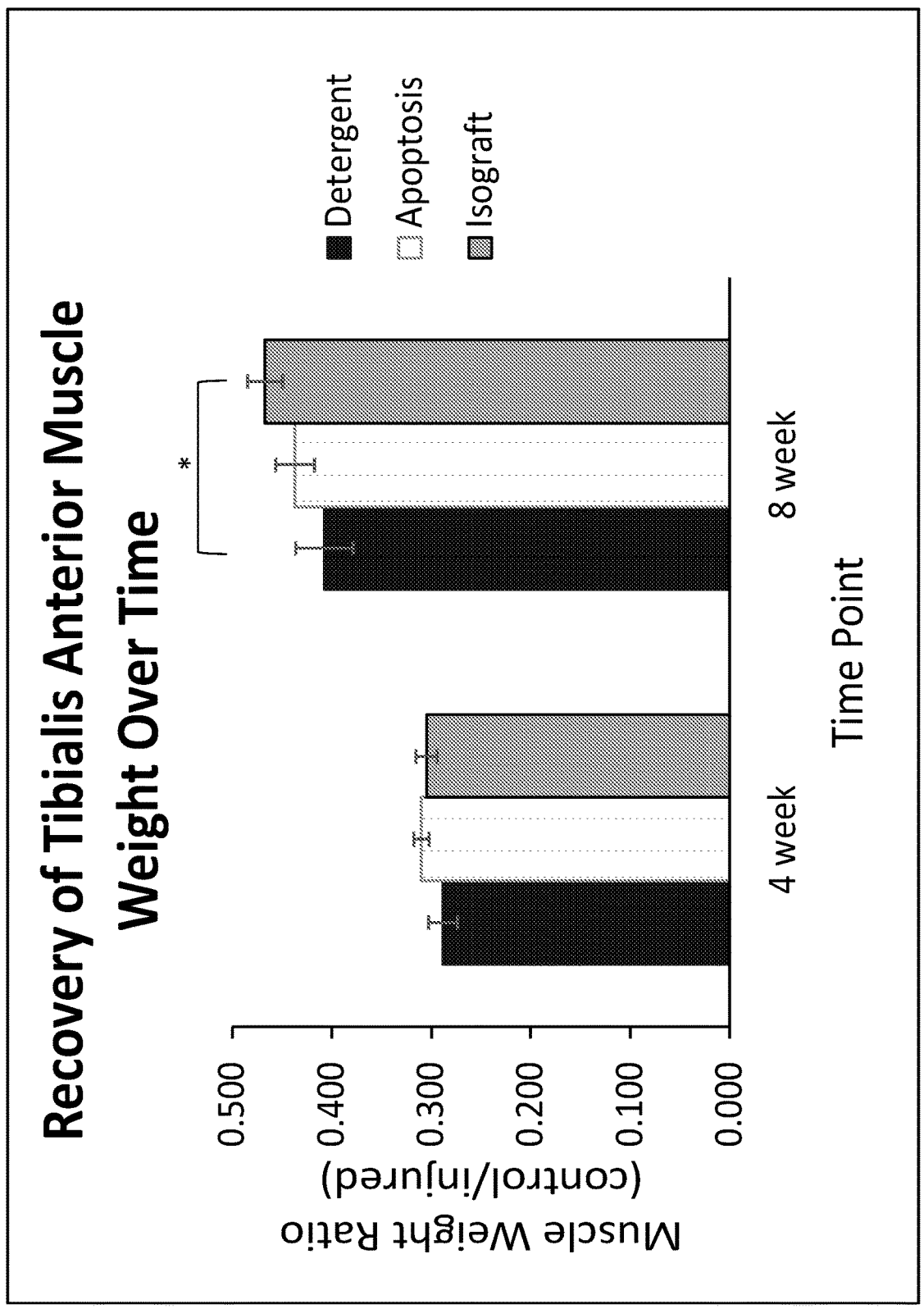
FIG. 8 shows a graph demonstrating tibialis anterior muscle weight changes over time in rats receiving detergent decellularized nerve graft, apoptosis decellularized nerve graft, or an isograft of fresh nerve. This figure demonstrates that the apoptosis decellularization method was not statistically different from isograft after 8 weeks, suggesting that the apoptosis decellularization method has the potential to perform similarly to the clinical gold standard and outperform traditional decellularization methods.

Results are shown in FIG. 8 and indicate that apoptosis decellularized samples enhance muscle recovery compared to detergent decellularized samples at both weeks 4 and 8, and are approaching levels of the isograft gold standard treatment. Throughout the time course of the study (2, 4, 6, and 8 weeks), animals were also recorded while walking on a track to analyze alterations in gait (data not shown). Histology was used to assess the degree of regeneration between groups at both 4 weeks and 8 weeks. (data not shown).

We claim:

1. A tissue decellularization method comprising:
   obtaining a tissue sample from a subject to generate an ex vivo tissue sample;
   exposing the ex vivo tissue sample to an apoptotic agent so as to produce apoptotic bodies; and
   washing the ex vivo tissue sample in a hypertonic solution so as to remove the apoptotic bodies and produce decellularized tissue.

2. The method of claim 1, wherein the tissue sample is a peripheral nerve, a nucleus pulposus, or a combination thereof or lung tissue.

3. The method of claim 1, wherein the apoptotic agent is camptothecin, staurosporine, doxorubicin, or an analog thereof.

4. The method of claim 1, wherein the concentration of the apoptotic agent ranges from about 1 nM to about 1 mM.

5. The method of claim 4, wherein the apoptotic agent is camptothecin, staurosporine, doxorubicin, or an analog thereof.

6. The method of claim 1, wherein the ex vivo tissue sample is exposed to the apoptotic agent for about 1-3 days.

7. The method of claim 1, further comprising the step of treating the ex vivo tissue sample with DNAse for a period of time ranging from about 30 minutes to about 24 hours.

8. The method of claim 1, wherein the step of washing produces an acellular tissue product.

9. The method of claim 8, further comprising the step of adding an active agent to the acellular tissue product.

10. The method of claim 9, wherein the active agent is selected from the group consisting of: a stem cell, a nucleic acid, an amino acid, a peptide, a polypeptide, an antibody, an aptamer, a ribozyme, a guide sequence for a ribozyme that inhibits translation or transcription of essential tumor proteins or genes, a hormone, an immunomodulator, an antipyretic, an anxiolytic, an antipsychotic, an analgesic, an antispasmodic, an anti-inflammatory, an antioxidant, an antihistamine, an anti-infective, a chemotherapeutic, or a combination thereof.

11. The method of claim 9, further comprising administering the acellular tissue product to a subject in need thereof.

12. The method of claim 8, further comprising administering the acellular tissue product to a subject in need thereof.

13. The method of claim 12, wherein the subject in need thereof has a spinal injury, a spinal disease, intervertebral disc degeneration, disease or trauma of the lungs, disease or trauma of the liver, volumetric muscle loss, peripheral nerve injury, amputation, spinal degradation, osteoarthritis of the hip, osteoarthritis of the knee, volumetric muscle loss, liver cirrhosis, or otherwise requires partial or total organ replacement, an antispasmodic, an anti-inflammatory, an anti-histamine, an anti-infective, a chemotherapeutic, or a combination thereof.

\* \* \* \* \*